(12) United States Patent
Steenbergen et al.

(10) Patent No.: US 6,224,969 B1
(45) Date of Patent: May 1, 2001

(54) OPTICAL PHANTOM SUITABLE FOR STIMULATING THE OPTICAL PROPERTIES OF BIOLOGICAL MATERIAL AND A METHOD OF PRODUCING SAID PHANTOM

(75) Inventors: Wiendelt Steenbergen, Enschede; Frits Frans Maria De Mul, Almelo; Jan Greve, Oldenzaal, all of (NL)

(73) Assignee: Stichting Voor de Technische Wetenschappen, Utrecht (NL)

( * ) Notice: Subject to any disclaimer, the term of this patent is extended or adjusted under 35 U.S.C. 154(b) by 0 days.

(21) Appl. No.: 09/143,706

(22) Filed: Aug. 28, 1998

(30) Foreign Application Priority Data

Sep. 1, 1997 (NL) .................................................. 1006902

(51) Int. Cl.$^7$ ............................. B32B 3/00; B32B 27/30; A61B 19/00; G01J 3/00
(52) U.S. Cl. .................................... 428/313.3; 428/313.5; 428/323; 428/327; 428/407; 128/897; 356/36; 356/128; 356/311
(58) Field of Search ................................. 428/313.3, 313.5, 428/313.7, 313.9, 323, 327, 314.2, 403, 407; 128/897; 356/36, 38, 311, 128; 524/503; 525/57

(56) References Cited

U.S. PATENT DOCUMENTS

| | | | |
|---|---|---|---|
| 4,762,495 | * | 8/1988 | Maloney et al. ..................... 434/271 |
| 5,141,973 | * | 8/1992 | Kobayashi et al. .................. 523/300 |
| 5,320,898 | * | 6/1994 | Yoshida et al. ...................... 428/195 |
| 5,366,801 | * | 11/1994 | Bryant et al. ......................... 428/283 |
| 5,423,996 | * | 6/1995 | Salyer ..................................... 252/70 |
| 5,633,584 | * | 5/1997 | Maryanski et al. .................. 324/300 |

FOREIGN PATENT DOCUMENTS 0243864   11/1987   (EP) .
0368436    5/1990   (EP) .

OTHER PUBLICATIONS

Alger, M.S.M., Polymer Science Dictionary, pp. 385–386, Apr. 1992.*

Encyclopedia of Polymer Science and Engineering, vol. 1; Additives, pp. 472–475, 1985.*

* cited by examiner

Primary Examiner—Paul Thibodeau
Assistant Examiner—Ramsey Zacharia
(74) Attorney, Agent, or Firm—Jeffrey D. Myers; Brian J. Pangrle

(57) ABSTRACT

The invention relates to an optical phantom that is suitable for simulating the optical properties of biological material and to a method of producing said phantom. The phantom is comprised of a matrix of poly(vinyl alcohol) (PVA) and spherical particles whose refractive index differs from that of the PVA. Preferably the PVA has a level of hydrolysis of >98%. Preferably the spherical particles are hollow polystyrene particles. In addition, light-absorbing and light-scattering substances may be added to the matrix.

12 Claims, No Drawings

OPTICAL PHANTOM SUITABLE FOR STIMULATING THE OPTICAL PROPERTIES OF BIOLOGICAL MATERIAL AND A METHOD OF PRODUCING SAID PHANTOM

The present invention relates to an optical phantom that is suitable for simulating the optical properties of biological material and to a method of producing said phantom.

Materials are known from practice, whose light scattering and light absorption levels are known. When said materials are used for the simulation of the optical properties of biological material, they are also called optical phantoms. To obtain light scattering in optical phantoms discreet particles are mixed with a transparent material, also called matrix, whose refractive index differs from the refractive index of the particles. Light absorption is realized by the addition of a dye.

The optical phantoms described in the literature up to date can generally be divided into the following categories:
- a mixture of a polymeric matrix and glass spheres or ceramic particles;
- a mixture of a matrix based on water and small fat globules (for example Intralipid®) or polymer spheres such as polystyrene. If desired, the particles may be fixed by adding gelatine.

There are, however, some disadvantages attached to the known optical phantoms of this type.

With the mixture of a polymeric matrix and glass spheres or ceramic particles, the attainable level of light scattering is limited because the refractive index of the glass differs little from that of the matrix, so that it is not possible to quantitatively represent, for example, human tissue. The arbitrary shape of the ceramic particles renders an accurate description of the scattering properties impossible. The addition of polymer spheres, for example polystyrene, to a polymeric matrix is problematic because dry polymer spheres are difficult to work with.

The phantoms comprising a mixture of a matrix on water basis and small fat globules or polymer spheres such as polystyrene, have a limited shelf life due to dehydration and fungal growth.

Moreover, with all the known phantoms it is very difficult or impossible to make layered structures that have a high vertical resolution. To simulate the stratification of skin tissue, a resolution of approximately 20–50 $\mu$m is required.

It is the objective of the present invention to remove these disadvantages. According to the present invention this objective is attained in that the optical tissue phantom is comprised of a matrix of poly(vinyl alcohol) (PVA) and substantially spherical particles whose refractive index differs from that of the PVA.

An important aspect of the phantom according to the present invention is that with this phantom a greater light scattering is possible than with the phantoms of the prior art which comprise a polymeric matrix, with the result that biological tissue can be quantitatively simulated. The shelf life is at least equal to that of the prior art phantoms on polymer basis. A further advantage is that it is simple to add polymer spheres, facilitating the quantitative description of the scattering properties and allowing stratified structures to be made, having a vertical resolution of approximately 20 $\mu$m.

In accordance with a further characteristic of the present invention, the PVA has a level of hydrolysis of 75–100 mole percent, preferably >98 mole percent. A wealth of literature about PVA indicates that PVA becomes less hydrophilic as the level of hydrolysis increases. Thus PVA with a higher level of hydrolysis absorbs less ambient moisture. As water absorption lowers the refractive index of the matrix, this is an important aspect for an optical tissue phantom. PVA with a high level of hydrolysis is preferred. In addition, when a PVA film is being manufactured it can be removed from the glass plate onto which it is cast more easily if the PVA has a higher level of hydrolysis.

In accordance with another characteristic of the present invention the diameters of the particles range from 0.45–1.5 $\mu$m, preferably from 0.9–1.2 $\mu$m.

In accordance with another favourable characteristic of the present invention the particles are hollow particles. When hollow particles are used, it is possible to attain a high level of light scattering.

In accordance with another characteristic of the present invention the hollow particles are filled with gas. By this means a high level of light scattering is attained.

In accordance with a further characteristic of the present invention the particles are polystyrene particles. Basically any small particles that can be suspended in water are eligible for use as particles with a different refractive index than that of PVA. These may include, for example, ceramic particles, glass spheres, polymethylene melamine, PMMA, polycarbonate, etc. Polystyrene is preferred, as polystyrene spheres of specific dimensions, which vary very little, are commercially available. This finally results in a homogenous film. Moreover, polystyrene is preferred to glass because polystyrene has a lower density than glass, which ensures that the film is more homogenous.

In accordance with a further characteristic of the present invention the optical tissue phantom also comprises a colourless solid. If, apart from the light-diffusing particles, another solid is added, the phantom becomes useful for the development and calibration of optical equipment by means of which the concentration of that same substance in, for example, tissue is measured.

In accordance with a further characteristic of the present invention the colourless solid is glucose. The use of glucose helps with the examination and calibration of optical techniques and medical equipment in which such techniques are applied when determining the glucose level of diabetics.

In accordance with another characteristic of the present invention the optical tissue phantom also comprises at least one light-absorbing substance. This allows the simulation of light absorption. Basically any water soluble dyes may be admixed. It is also possible to use a mixture of several light-absorbing substances. The absorption spectrum is a linear combination of the absorption spectra of the separate dyes. The narrower the absorption peaks of the separate dyes, the greater the freedom in choosing an absorption ratio in the mixture applying for specific wavelengths. For skin tissue the absorption ratio between 780 nm, 630 nm and 540 nm is approximately 1:2:3. Thus this can be simulated by making a suitable mixture of three dyes.

In accordance with another characteristic of the present invention the light absorbing substance is Talens Ecoline® paint. The advantage of Talens Ecoline® paint is that it does not comprise any solid pigment; in other words, Talens Ecoline® paint only absorbs without diffusing. This is not the case with Indian ink, which is slightly light-diffusing.

The present invention also relates to a method of producing an optical tissue phantom, characterized in that PVA is dissolved in an aqueous solvent, whereafter substantially spherical particles having a refractive index different to that of PVA are added to the solution, the thus obtained mixture is cast onto a substantially flat surface and the solvent is evaporated.

According to the invention, PVA is conveniently dissolved at a temperature of 20° C.–100° C., preferably at 95° C.–100° C. The temperature above which PVA dissolves in water depends on the level of hydrolysis. The preferred PVA, i.e. one having a high level of hydrolysis, dissolves at a temperature of 95° C. or higher.

According to another characteristic of the present invention, PVA having a level of hydrolysis of 75–100%, preferably >98%, is dissolved.

According to another characteristic of the present invention, the concentration of PVA added to the solvent is 1–15% by weight and preferably 8–12% by weight. This provides a workable solution.

According to another characteristic of the present invention the solvent for PVA is water. Other possible solvents for PVA include, for example, DMSO, acetamide, glycols, DMF, glycerol, piperazine, triethylene diamine, formamide and HMTP. Solution in water is preferred, as this facilitates admixing aqueous suspensions of the light-diffusing particles.

According to another characteristic of the present invention the diameter of the particles ranges from 0.45–1.5 $\mu$m and preferably from 0.9–1.2 $\mu$m.

According to another characteristic of the present invention the particles are hollow particles.

According to another characteristic of the present invention the hollow particles are filled with gas.

According to another characteristic of the present invention the gas is air.

According to another characteristic of the present invention the particles are polystyrene particles.

According to another characteristic of the present invention a colourless solid is also added prior to casting the mixture.

According to another characteristic of the present invention said colourless solid is glucose.

According to another characteristic of the present invention at least one light-absorbing substance is also added to the mixture prior to casting.

According to another characteristic of the present invention said light-absorbing substance is Talens Ecoline® paint.

The present invention will now be explained in more detail with reference to a few exemplary embodiments.

EXAMPLE I

Optical tissue phantom of PVA having a level of hydrolysis of 99$^+$% comprising hollow polystyrene (PS) spheres having a diameter of 1 $\mu$m and a shell thickness of 0.1 $\mu$m.

A 1-liter flask, in a water bath with heating plate/magnetic agitator, provided with a agitation magnet was filled with 1000 ml demineralized water. While stirring, 110 g. dry PVA (level of hydrolysis: 99$^+$%, molecular weight: 85,000–146,000, available from Aldrich) was added. The flask was then sealed with foil. The flask was heated in the water bath to 95° C. The flask was left to stand for 30 minutes at 95° C. until the PVA was dissolved and the solution had become clear. Then stirring commenced lasting approximately 15 minutes until most of the air bubbles had escaped from the solution. After cooling to approximately 45° C., the solution was transferred to 50-ml centrifugal tubes. The solution was centrifuged for 30 minutes at 35° C. at 2,500×g. The result is a clear PVA solution: the bubbles have escaped via the surface of the solution or have accumulated at the top in the solution and can be simply skimmed off. The tubes containing the PVA solution were stored in the refrigerator. Prior to production of the film, the solution was reheated in a water bath until it was liquified again. The solution was then cooled to room temperature. In a laminar flow cabinet with horizontal efflux of dust-free air a 12 mm-thick glass plate (window glass) was placed onto an aluminium plate resting by means of four exact adjusting grooves on the base of the laminar flow cabinet. The glass plate was scrupulously cleaned with ethanol and subsequently with acetone. Using a pipet, a 5% suspension of PS spheres was added to the PVA solution. The mixture of PVA solution and PS speres was centrifuged for 10 minutes at room temperature at 2,500×g. Any air bubbles floating on the mixture were optionally skimmed off and the mixture was carefully cast onto the glass plate. With the aid of a spreader which was driven at a constant speed (9 mm/s), the mixture was spread to form a thin even layer. After casting, the glass plate remained in the laminar flow cabinet, until the film was dust-dry. Subsequently the film was allowed to continue drying in a nitrogen-ventilated cabinet. The film was then readily removed from the plate. The thickness of the film was 50 $\mu$m.

EXAMPLE II

Optical tissue phantom of PVA having a level of hydrolysis of 99$^+$% comprising solid PS spheres having a diameter of 1.16 $\mu$m.

The method of Example I was repeated but the suspension of PS spheres was a 2.5% suspension and the solid weight fraction was 0.025 g. per ml suspension. The film had a slightly blue tint and, compared with Example I, it was much more transparent.

EXAMPLE III

Optical tissue phantom of PVA having a level of hydrolysis of 99$^+$% comprising hollow PS spheres having a diameter of 1 $\mu$m and a shell thickness of 0.1 $\mu$m and a dye concentrate.

The dye concentrate was metered out as follows: 0.818 mg IRA WS1 per 1 g. of demineralized water, 22,2 mg dark-green Talens Ecoline® paint per 1 g. of water and 40.2 mg carmine Talens Ecoline® paint per 1 g. of water. IRA WS1 (available from Zenica Specialties, Manchester, Great Britain) exhibits an absorption peak at 780 nm and is supplied as a dark-green powder, which dissolves very well in water. The method of Example 1 was followed, and the dye concentrate was added simultaneously with the PS suspension. The film obtained had a slightly purple tint. The absorption the film exhibited for 544 nm, 633 nm and 780 nm is comparable with that of skin tissue.

EXAMPLE IV

Optical tissue phantom of PVA having a level of hydrolysis of 88% (Aldrich Mowiol® 4088) comprising hollow PS spheres having a diameter of 1 $\mu$m and a shell thickness of 0.1 $\mu$m.

The film did not very readily come off the glass plate. The following method was therefore applied:

drying for 8 hours by blowing air over it;

swelling for 5 hours in humid atmosphere: a sealed box containing several water vessels;

drying for 5 hours by blowing nitrogen over it;

the film is cut loose at the edge with the aid of a scalpel and pulled off the plate. The optical appearance of the film is the same as in Example I. However, humidity influences both the optical and the mechanical properties much more than with 99$^+$% PVA. Therefore 99$^+$% is preferred.

EXAMPLE V

Optical tissue phantom of PVA having a level of hydrolysis of 99%, comprising glucose in a quantity occurring in the human body, and hollow PS spheres having a diameter of 1 µm and a shell thickness of 0.1 µm.

The method of Example I was followed. The $D^{(+)}$-glucose (M=180.16 g/mol, available from Merck) was added immediately after the PS suspension. 1 g. of a glucose solution of 0.203 g. in 10 g. demineralized water was added. The ultimate glucose concentration was 450 mg/dl of phantom. This is the maximum concentration occurring in diabetes patients. The phantom exhibited no difference in quality or appearance in comparison with that of Example I.

EXAMPLE VI

Optical tissue phantom produced nine months earlier in accordance with Example III The quality of the film has not deteriorated, which proves that the phantom has a long shelf life.

What is claimed is:

1. An optical tissue phantom that is suitable for simulating the optical properties of biological material, characterized in that the optical tissue phantom comprises a film comprising a matrix of poly(vinyl alcohol) (PVA) and substantially spherical particles whose refractive index differs from that of the PVA.

2. An optical tissue phantom according to claim 1, characterized in that the PVA has a level of hydrolysis of 75–100 mole percent.

3. An optical tissue phantom according to claim 1, characterized in that the PVA has a level of hydrolysis of greater than 98 mole percent.

4. An optical tissue phantom according to claim 1, characterized in that the diameter of the particles ranges from 0.45–1.5 µm.

5. An optical tissue phantom according to claim 1, characterized in that the particles are hollow particles.

6. An optical tissue phantom according to claim 5, characterized in that the hollow particles are filled with gas.

7. An optical tissue phantom according to claim 6, characterized in that the gas is air.

8. An optical tissue phantom according to claim 1, characterized in that the particles are polystyrene particles.

9. An optical tissue phantom according to claim 1, characterized in that the optical tissue phantom also comprises a colourless solid.

10. An optical tissue phantom according to claim 9, characterized in that the colourless solid is glucose.

11. An optical tissue phantom according to claim 1, characterized in that the optical tissue phantom also comprises at least one light-absorbing subatance.

12. An optical tissue phantom according to claim 11, characterized in that the light-absorbing substance is paint.

* * * * *